United States Patent
Pawluczyk et al.

(10) Patent No.: US 6,928,311 B1
(45) Date of Patent: Aug. 9, 2005

(54) COMPACT DEVICE FOR MEASURING, TISSUE ANALYTES

(75) Inventors: Romauld Pawluczyk, Conestogo (CA); Duncan Macintyre, Campbellville (CA); Bronislaw Bednarz, Toronto (CA)

(73) Assignee: NIR Diagnostics Inc., Ontario (CA)

( * ) Notice: Subject to any disclaimer, the term of this patent is extended or adjusted under 35 U.S.C. 154(b) by 0 days.

(21) Appl. No.: 10/070,191

(22) PCT Filed: Aug. 31, 2000

(86) PCT No.: PCT/CA00/01004

§ 371 (c)(1),
(2), (4) Date: Jun. 3, 2002

(87) PCT Pub. No.: WO01/15595

PCT Pub. Date: Mar. 8, 2001

Related U.S. Application Data (60) Provisional application No. 60/151,538, filed on Aug. 31, 1999.

(51) Int. Cl.[7] ............................................. A61B 5/00
(52) U.S. Cl. ........................ 600/310; 600/322; 600/473
(58) Field of Search ............................... 600/310, 316, 600/322, 323, 473; 356/39, 300, 319, 320, 356/326, 328; 250/339.01, 339.02, 339.05, 250/339.06, 339.07, 339.11, 339.12, 340, 250/341.1, 341.2, 341.8

(56) References Cited

U.S. PATENT DOCUMENTS

| | | | |
|---|---|---|---|
| 5,086,229 A | | 2/1992 | Rosenthal et al. |
| 5,167,230 A | | 12/1992 | Chance |
| 5,361,758 A | | 11/1994 | Hall et al. |
| 5,429,128 A | | 7/1995 | Cadell et al. |
| 5,553,613 A | * | 9/1996 | Parker ......................... 600/322 |
| 5,701,894 A | * | 12/1997 | Cherry et al. ............... 600/300 |
| 5,830,132 A | * | 11/1998 | Robinson .................... 600/322 |
| 6,078,828 A | * | 6/2000 | Yasuda et al. .............. 600/310 |
| 6,159,147 A | * | 12/2000 | Lichter et al. .............. 600/323 |

FOREIGN PATENT DOCUMENTS

WO  9200513  1/1992

\* cited by examiner

Primary Examiner—Eric F. Winakur
(74) Attorney, Agent, or Firm—Hovey Williams LLP (57) ABSTRACT

A compact device (20) for non-invasively monitoring concentration levels of blood constituents, including glucose, cholesterol, alcohol, blood gases and various ions. The device includes a finger receptor (140) having a channel for receiving a finger of a user. The channel has a light entrance and a light exit so that light can be passed from a light source (91) through a finger located in the channel in a direction generally normal to the finger. Certain heat generating components, including a stable power supply for the device, are external to the device housing so as to reduce heat generation and thereby increase stability of the device. The device includes a communications interface for interacting with a computer. The device can be used for clinical use or for home use and the memory of the computer can be used to assist with record keeping and with dosage calculations.

12 Claims, 6 Drawing Sheets

COMPACT DEVICE FOR MEASURING, TISSUE ANALYTES

This application claims the benefit of provisional application Ser. No. 60/151,538, filed Aug. 31, 1999.

FIELD OF THE INVENTION

This invention relates to a compact device for non-invasively measuring concentration levels of blood constituents. The device includes a communications interface for interacting with a computer.

BACKGROUND OF THE INVENTION

Invasive techniques of measuring blood constituents are in common usage. These techniques are painful, potentially dangerous and expensive to operate. The normal procedure is to obtain a blood sample from a vein and this sample is then tested in a medical laboratory, using a number of chemical procedures to measure each constituent separately. Alternatively, home glucose testing uses a finger puncture that is spotted onto an enzyme-based semi-permeable membrane test strip and is allowed to react for a certain length of time, with insulin administration then based upon either a visual color comparison with a standard color chart or by means of a more accurate and unambiguous spectroscopic technique (for example by measurement and comparison of reflectance at several wavelengths). There is a risk of infection and sometimes a patient can develop a rash when these invasive techniques are used.

Previous devices for non-invasively monitoring concentrations of blood constituents of a patient are also known. These devices are used to externally measure either the concentration of the constituent in gases emitted by the body; the concentration contained in perspiration; or the concentration contained in body fluids such as tears, saliva, or urine samples; or, alternatively, the blood constituent is measured using radiation passed through a part of the patient's body such as the earlobe or finger.

A recently developed and patented non-invasive method and device is described in U.S. Pat. No. 5,361,758. '758 discloses a non-invasive method and device for monitoring the concentration levels of one particular constituent or, alternatively, of measuring the concentration level of several different constituents simultaneously, the method and device producing results in a short time period that are highly accurate and compare favorably to invasive techniques.

Specifically, the non-invasive device and method disclosed in '758 measures concentration levels of blood and tissue constituents in a living subject such as a human or animal utilizing a polychromatic light source that emits light over a broad spectrum of wavelengths in the near infrared range. The light is passed through, or reflected from, a part of the subject such as a finger, ear lobe or other part of the body. That light is then separated into its various components by means of a grating or prism, and the near infrared band is focussed onto a linear array detector. A microprocessor uses the output of the array detector to measure the transported light (scattered light and possibly transmitted light), calculate the equivalent absorbance, and calculate the second derivative of the equivalent absorbance. A calibration equation is used for each constituent to be monitored to convert the second derivative measurements to a concentration level for that constituent. The device can be used to determine levels of various blood and tissue constituents, including glucose, cholesterol, alcohol, blood gases and various ions.

A finger receptor for use with a non-invasive monitoring device such as the one described '758 is disclosed in U.S. Pat. No. 5,429,128. The finger receptor disclosed in '128 has a channel for receiving a finger of a user. The channel has a light entrance and a light exit so that light can be passed from a light source through a finger located in the channel in a direction generally normal to the finger. Extraneous light is excluded and the finger is held in position by a spring-mounted roller. The receptor has sensing means to determine when a finger has been properly positioned in the channel.

While the method and devices disclosed in '758 and '128 provide a significantly improved and effective non-invasive technique for monitoring the concentration of known constituents in blood or tissue, there is a need for a device which is compact, efficient and portable, and which has improved stability and less sensitivity to problems created by heat.

SUMMARY OF THE INVENTION

It is an object of the present invention to provide a device for non-invasively monitoring concentration levels of blood constituents, the device being compact and efficient, and having improved stability and reduced sensitivity to heat. The device includes a communications interface for interacting with a computer and draws power from a stable external power supply.

In one aspect, the present invention provides a measuring device for non-invasively measuring levels of constituents in blood and tissue in a living subject such as a human or animal, said measuring device comprising:

(a) a polychromatic light source that emits a broad spectrum of light in the near infrared range and adjacent visible light;

(b) a part receptor shaped for receiving a part of said subject, said part receptor being located relative to said light source so that when part of said subject is placed in the part receptor, said light source can be activated and light from said light source can be directed onto said part;

(c) a light receptor for collecting a continuum of wavelengths over said broad spectrum after said light has been directed onto said part;

(d) dispersion means coupled to said light receptor for dispersing said collected light into a dispersed spectrum of component wavelengths of said collected light;

(e) a photodetector coupled to said dispersion means for taking absorbance measurements from said dispersed spectrum and producing a measurement signal;

(f) a communications interface connectable to an external computer for communicating said measurement signal to said computer; and (g) a power interface connectable to an external stabilized power source.

Preferably, the polychromatic light source is connected to the external stabilized power source through said power interface.

More preferably, the external computer controls at least one function of said compact measuring device, said computer including means for receiving said measurement signal.

More preferably, the device further includes an analog to digital converter for converting said measurement signal into a digital measurement signal for communication to said computer.

Preferably, the external computer includes a memory, a storage, and software means for storing a plurality of said measurement signals for a plurality of measurements.

Also preferably, the external computer includes a memory, a storage, and software means for storing, retrieving and displaying dosage information corresponding to measurement signals received by said computer from said device.

More preferably, the external stabilized power source is provided by said external computer.

BRIEF DESCRIPTION OF THE DRAWINGS

For a better understanding of the present invention, and to show more clearly how it may be carried into effect, reference will now be made, by way of example, to the accompanying drawings which show a preferred embodiment of the present invention, in which.

DETAILED DESCRIPTION OF A PREFERRED EMBODIMENT

As noted above, this invention relates to a compact device for non-invasively measuring concentration levels of blood constituents.

The basic principles of operation of the non-invasive measurement technique used in the present invention is provided in U.S. Pat. No. 5,361,758 which is incorporated herein by this reference.

'758 discloses that a near infrared region of the electromagnetic spectrum is particularly well-suited to in vivo diagnostic applications because human tissue is essentially transparent to the incident radiation and therefore sufficient penetration of the radiation is possible to allow accurate quantitative analysis.

Figure 1:
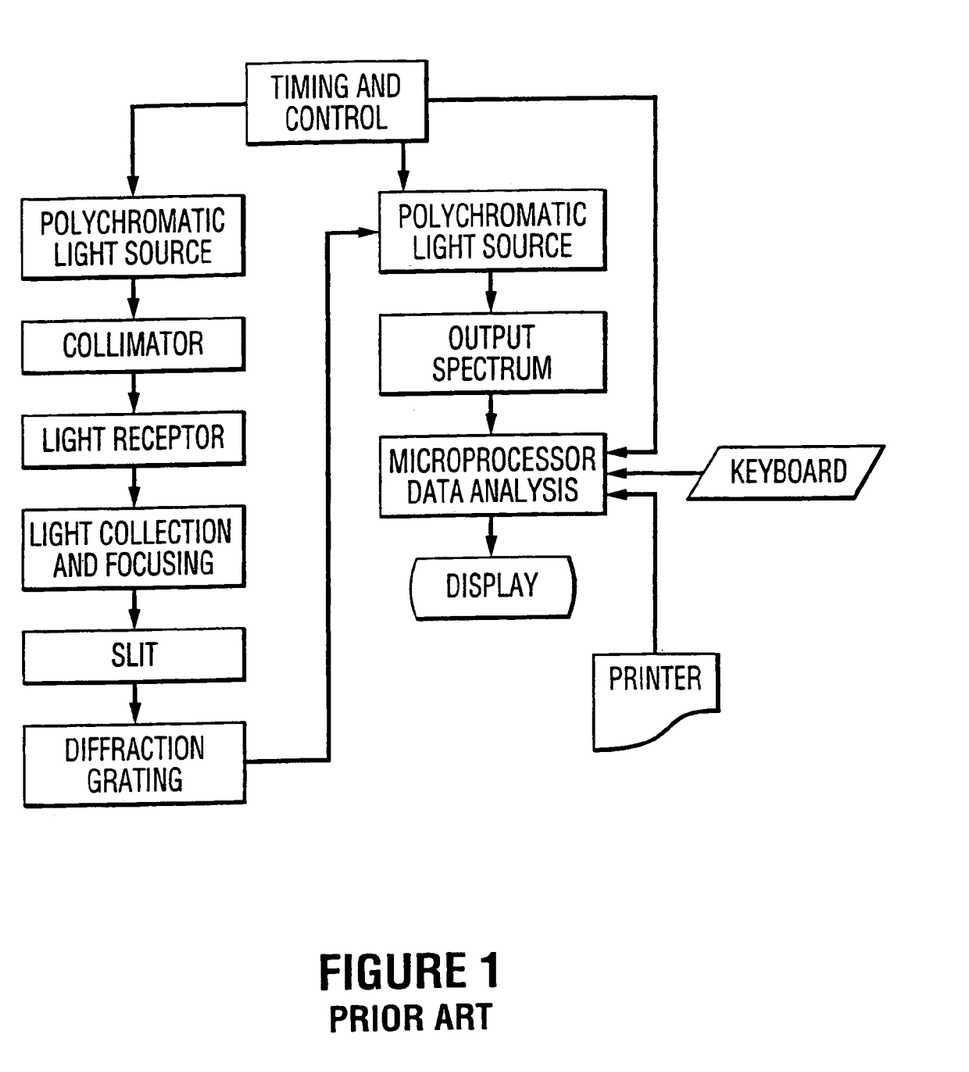
FIG. 1 is a block diagram showing the relationships for various components of a device for non-invasively monitoring the concentration levels of blood constituents.

As shown in FIG. 1, a prior art non-invasive device for continuously monitoring concentration levels of blood and tissue constituents has a polychromatic light source. '758 discloses that the light source can emit light over a very wide bandwidth including light in the near infrared spectrum. (It has been recognized by the inventor that adjacent visible light outside of the range specified in '758 also contributes information for in vivo diagnostic applications.) The light from the light source passes first through a collimator, which is a collection of lenses that concentrate the light into a narrow parallel beam directed at the receptor. The receptor is shaped to receive within it a part of the subject, for example, a finger or ear of a human. The light is directed onto the finger or ear and is scattered and attenuated by the finger or ear. The scattered and attenuated light is collected by lenses and directed through a slit to diffraction means. Preferably, the diffraction means is a diffraction grating, possibly produced with holographic method. The light from the grating is dispersed into its component wavelengths so that it falls along the length of a linear array detector. The array detector has a series of photosensitive elements, which are electronically scanned by a microprocessor to measure the intensity of light for each wavelength transmitted through or reflected from the tissue in the receptor. The detector is connected to the microprocessor, producing an output spectrum, with the microprocessor analyzing the measurements and ultimately producing a result for each concentration level determined. The result can be shown on a display and/or printed on a printer. The keyboard allows a user to control the device, for example, to specify a particular constituent to be measured. The timing and control is activated by the microprocessor to control the device, for example, to determine number and timing of measurements.

It is disclosed in '758 that the polychromatic light source can be a tungsten-halogen bulb and is powered by a stabilized power source, for example, a DC power supply, or by a battery. (The inventors have realized that photoluminescent sources of radiation may also be used.) This polychromatic light source may be a tungsten-halogen lamp or it may be a collection of LEDs or other light sources selected to emit radiation in the near infrared region (and adjacent visible light, as realized by the inventors). It should be noted that after activation of the light source, the scanning detector is read so that light is passed through the receptor and measured by the detector through the taking of a series of measurements at a selected wavelength.

In the system disclosed in '758, the microprocessor control activates and scans the linear array detector only after a detected pulse has occurred and the full spectrum measurements are then taken for the light after it passes through the receptor. Scanning is stopped when another pulse is detected on the selected wavelength. In other words, measurements are taken only when the blood pressure in the finger or ear or other part of the person is at a constant level.

In contrast, in the present invention, measurements are taken over some phase of a pulse, or are taken over several pulses, and an average of the resulting signal over the measurement period is calculated.

It is explained in '578 that in a further variation, the device can take all measurements regardless of the pulse of the subject. The microprocessor can then be controlled by computer software to select those measurements that are taken between pulses and to base the calculation of the concentration levels on the selected measurements. In a further variation, the measurements upon which the results are based, could be taken during pulses.

It is explained in '758 that the receptor has means for eliminating extraneous light. For example, where a finger is the part of a human through which the light passes, the receptor has an oblong shape similar to but larger than the shape of the finger. The means for eliminating extraneous light from the receptor is a flexible ring that surrounds an entrance to the receptor. When the finger is inserted, the flexible ring forms a seal around the finger when the finger has been inserted into the receptor. All surfaces within the device, including surfaces within the receptor are made non-reflective to minimize stray light. (The flexible ring forming the seal is optional and is not used in the present invention. However, measures have been taken to minimize stray light, as discussed further below.)

Finally, '758 discloses that, after the measurements are taken with a finger of the subject in place in the finger receptor, a reference set of measurements is taken of the incident light, being the light generated in the device when no part of the subject is in contact with the receptor. A ratio of the two measurements is then calculated.

Figure 2:
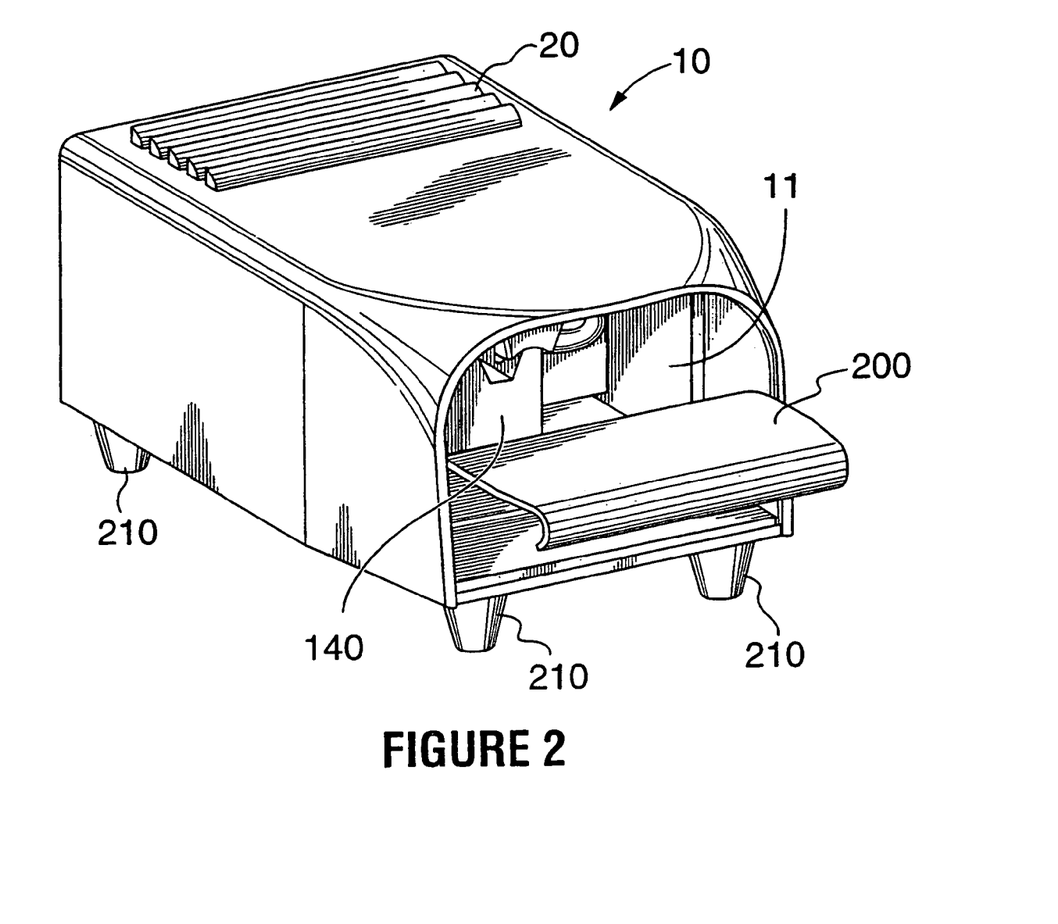
FIG. 2 is a perspective view of one embodiment of a device in accordance with the present invention.

Based on the principles of operation of a non-invasive monitoring device summarized above and disclosed in detail in '758, a new and improved compact device for non-invasively monitoring the concentration levels of blood constituents is shown in FIG. 2 and generally referred to by reference numeral 10. FIG. 2 shows an external perspective view of the device 10 with an instrument cover or housing 20 and a hand support 200, and shows an opening 11 into which the hand of a user is inserted for taking a measurement of the user's blood or tissue constituents. Optional legs 210 allows the device 10 to sit in position on a flat surface.

Figure 3A:
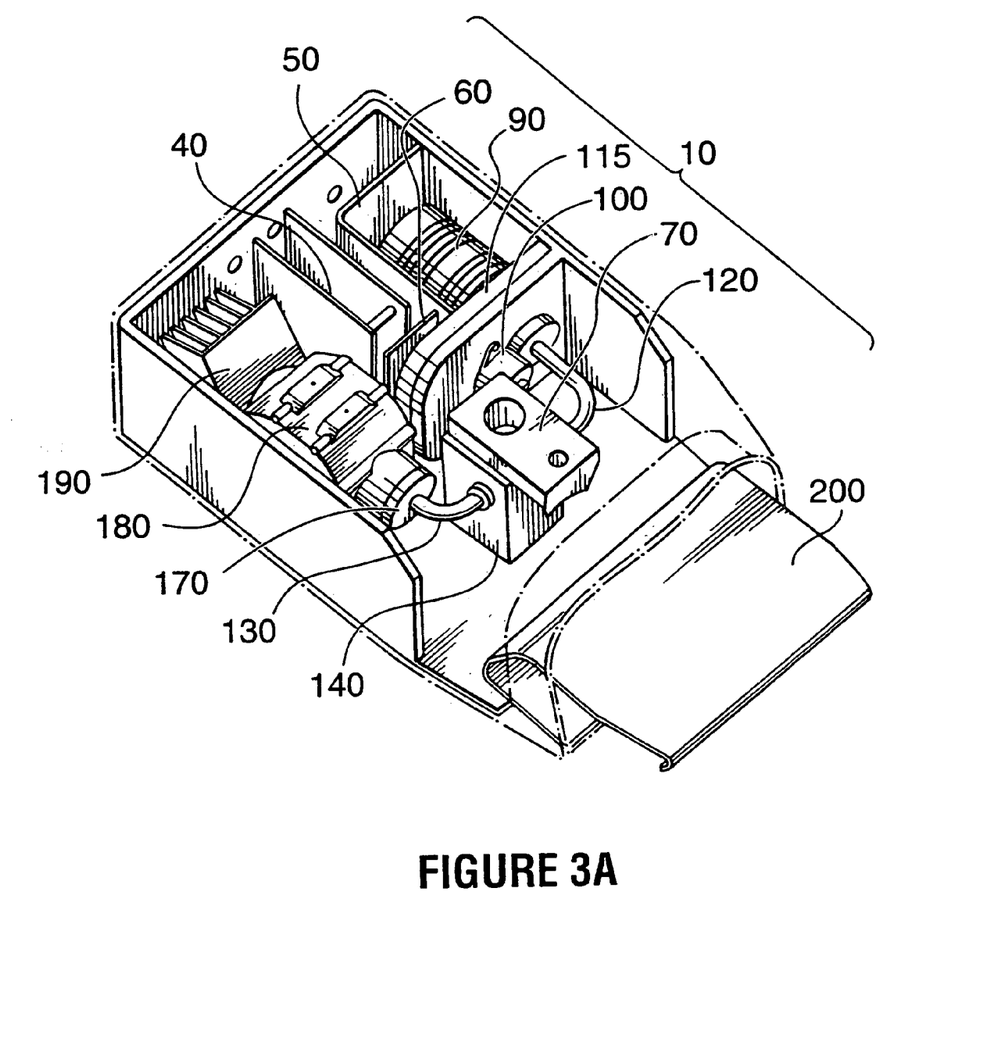
FIG. 3A is another perspective view of the device of FIG. 2 showing some of the internal components of the device.
Figure 3B:
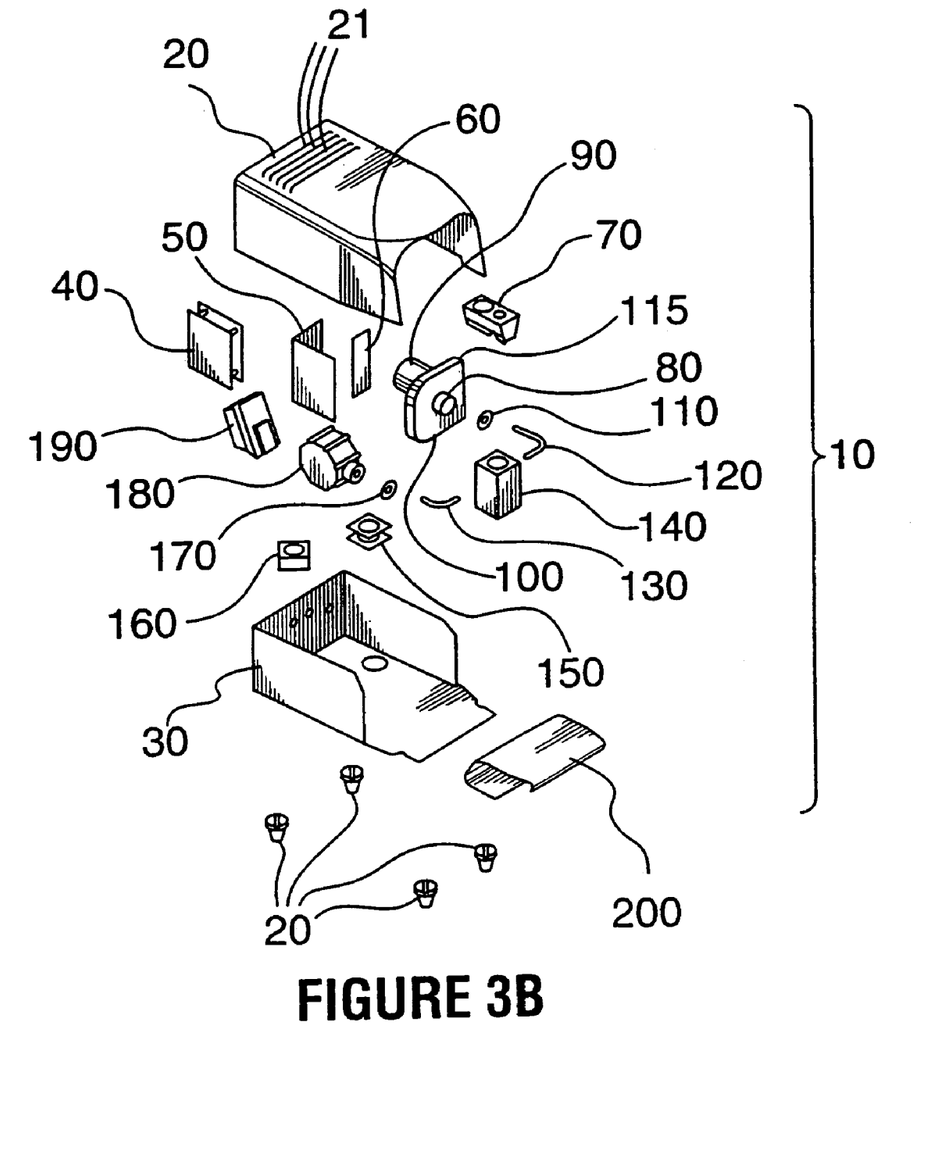
FIG. 3B is an exploded view of the device of FIG. 2, also showing the internal components of FIG. 3A.
Figure 3C:
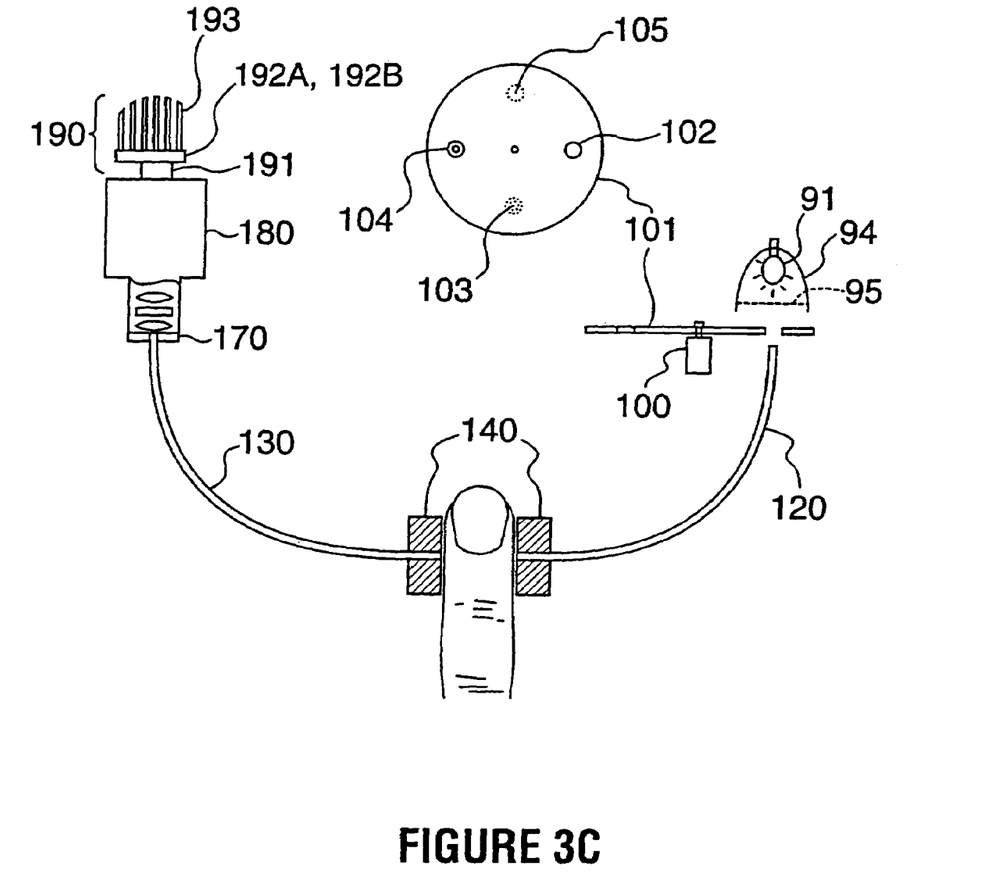
FIG. 3C shows a schematic view of some of the main components of the device shown in FIGS. 3A and 3B.

Now referring to FIGS. 3A–3C, and referring back to FIG. 1, there is provided a polychromatic light source which may comprise a lamp 91 (FIG. 3C) within a lamp housing or reflector 94 (FIGS. 3A and 3B). The light source or lamp 91 in FIGS. 3A and 3B is able to generate light over a wide bandwidth including the near infrared regions, discussed earlier, and further including adjacent visible light.

While the '758 patent discloses the use of a collimator (FIG. 1) which uses a series of lenses to concentrate the light from the polychromatic light source into a narrow parallel beam, the present invention uses an elliptical reflector 94 to reflect and concentrate the light from the polychromatic light source or lamp 91. A heat reflection filter 95 is provided within the elliptical reflector 94 to contain heat generated by the lamp 91.

Still referring to FIGS. 3A–3C, a multi-positional shutter 101 is provided between the lamp 91 and the first light guide 120 to further control the light entering the first light guide 120, or otherwise filtering, attenuating, or blocking the light entering the first light guide 120. A stepping motor 100 is provided for rotating the multi-positional shutter 101 into one of a plurality of rotational positions. In one position, the multi-positional shutter 101 provides an opening 102 to allow light concentrated by the elliptical reflector into a first light guide 120. In another position, a plurality of very small holes 103 are provided to allow some of the light from the light source 91 to enter the first light guide 120. In yet another position, a filter 104 is provided which attenuates the light from the light source 91 entering the first light guide 120. In yet another position 105, the multi-positional shutter 101 entirely blocks the light from the light source 91. Various other means of attenuating or otherwise controlling the light entering the first light guide 120 may be provided on the multi-positional shutter 101.

Still referring to FIGS. 3A–3C, a the first light guide 120 guides the beam of light to a finger receptor 70, 140. The operation of the finger receptor 70, 140 is described in detail in U.S. Pat. No. 5,429,128 which is incorporated herein by this reference. As disclosed in '128, the finger receptor 70, 140 receives a finger of a user into a channel, and the beam of light guided by the first light guide 120 is directed generally normally to the finger inserted into the finger receptor 70, 140. As further disclosed in '128, and described above, the finger receptor 70,140 includes a sensing means to determine when a finger had been properly positioned in the channel and acts to exclude extraneous light which would interfere with the signal received by the light receptor (FIG. 1). In order to further reduce the amount of extraneous light entering the light receptor (FIG. 1), the device cover 20 has been designed to substantially cover the finger receptor and other components within the device housing 20, 30. Referring back to FIG. 2, preferably, the hand support 200 may be adjustable preferably in a vertical direction so as to adjust the size of the opening 11 to accommodate hands of different size. Also, the top of the opening 11 may be shaped to generally fit the profile of a human hand across the top of the hand, so that extraneous light entering the housing 20 is minimized. It will also be appreciated that the edges of the opening 11 may be somewhat flexible to better fit the shape of an inserted hand.

Light which passes through the finger receptor 70, 140 is received by a light receptor (FIG. 1) which in FIGS. 3A and 3B comprises a second light guide 130 which guides light to a light guide adapter 170 and to a spectroscope 180. The light is then detected by a thermostabalized and/or cooled photodetector array assembly 190 which includes a photodetector array 191, electronics 192A to control a thermoelectric cooler and electronics 192B to digitize the signal received by the photodetector array 191, and a heat sink 193 including a thermoelectric cooler to dissipate heat.

Preferably, the electronics in the photodetector array assembly 190 provides analog to digital conversion of the light signal received by the photodetector array 190 for transmission to a computer. Sending an analog signal to a computer for processing and conversion is less preferred since an analog signal is more susceptible to electromagnetic interference. As explained earlier, the device 10 shown and described in FIGS. 3A and 3B (and shown in block diagram form in FIG. 1) requires stable operating conditions to function optimally. One component which is important to stability of the device 10 is a stable power supply with a large power reserve.

In previous devices, such a power supply is typically provided within the device, and the heat generated by the power supply and other internal components has the potential to affect the stability and accuracy of the device.

Figure 4:
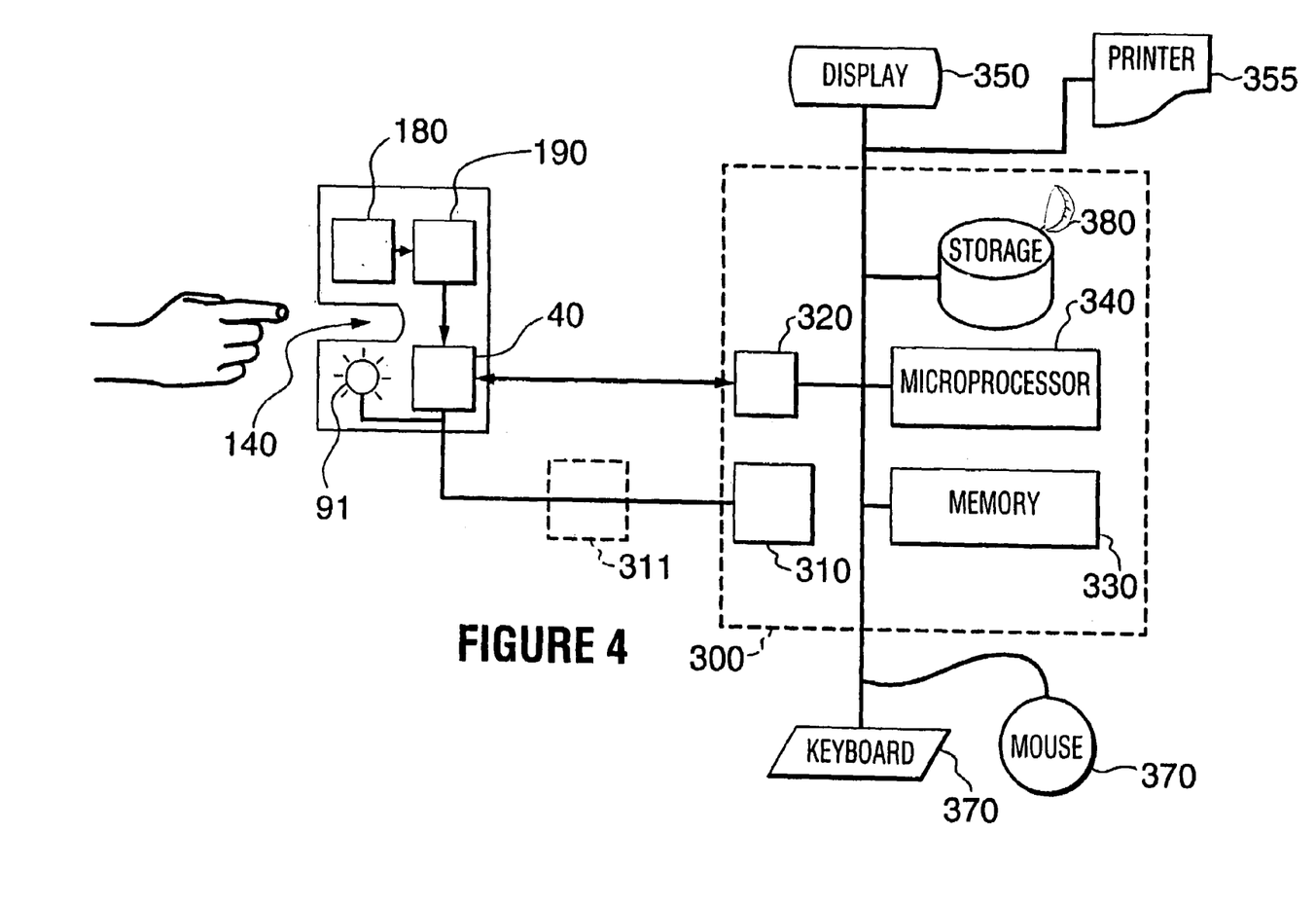
FIG. 4 is a block diagram showing the relationships between the device of FIGS. 2, 3A–3C and a computer system.

In order to provide a compact, high-performance device with improved stability, the device 10 shown and described in FIGS. 2 to 4 operates on a power supply which is external to the device 10. As the device 10 is designed to interface with a computer 300 ((FIG. 4), preferably, the device 10 will draw power from the computer power supply 310. A power conditioner 311 may be provided between the computer power supply 310 and the device 10 in order to provide a stable, clean power source for the device 10.

Referring back to FIGS. 3A–3C, the component which will generate the most heat within the device is the lamp within the lamp housing 90. In order to minimize the effect of the heat generated by the lamp and lamp housing 90, a lamp heat screen 50 is provided between the lamp housing 90 and the other components in the device, including the electronics 40, the spectroscope 180 and the photodetector array 190. Furthermore, an electronics board 60 to control the multi-positional shutter 101 also provides a shield to the electronics 40 from the heat conducted by the multi-positional shutter housing 115 from the lamp 91.

Advantageously, by shielding the heat generating lamp housing 90 from the other components in the device, and by removing the power supply so that the power supply is external to the device (preferably the computer power supply 310), the heat generated within the device housing 20, 30 is significantly reduced. Heat which is produced within the housing 20, 30 is dissipated by the heat sink provided with the photodetector array 190 and is also removed from the device housing 20, 30 by means of cooling fans 150 and 160 and vents 21.

As a result of the heat generated in the housing 20, 30 being significantly reduced, and as a result of the reduced electronic noise in the electronic circuits in the device 10, a less powerful light source can be used in the device 10. That is, the lamp (tungsten-halogen lamp) used for the light source may be less powerful while the same level of measurement sensitivity is retained (because of the lower noise level in the electronic circuits) as compared to a device with an internal power supply.

Also, by allowing the computer 300 (FIG. 4) interconnected to the device 10 to process many of the control functions for the device 10, the electronics 40 required within the device 10 can be minimized to basic control and communications functions. In effect, the device 10 may then be operated as if it was a peripheral device to a computer, with the main function of the device 10 being for providing a light source, a light receptor, and providing raw data resulting from the measurement for further processing.

In a preferred embodiment, the device 10 is interconnected to a computer by means of a customized computer interface card 320. For example, the computer interface card 320 may be built to interconnect with an industry standard PCI (Peripheral Circuit Interconnect) bus or an ISA (industry standard architecture) bus, both of which are common to many personal computer systems presently available, or any other bus developed for computer interface in the future. For use with a portable laptop computer system, a suitable customized computer interface card may be developed to the PCMCIA industry standard. The computer interface card 320 may receive analog data from the device 10 and covert the analog signal to a digital signal for processing by the computer 300.

A connection for the device 10 via other industry standard interfaces such as parallel or serial ports, SCSI and USB ports is also possible, although such options may require additional electronics to be placed within the device housing 20, 30 and thus increase the heat generation within the device 10. Nevertheless, a benefit of such a connection to a parallel, serial, SCSI or USB port is that the installation of a card into a computer may not be required.

As explained, the interconnection of the device 10 to a computer 300 facilitates controlling the device 10 using software means running in memory 330 and the microprocessor 340 and optionally stored in storage 380 in the computer 300. Furthermore, the software means may provide a user with a graphical user interface on a suitable display 350 including step-by-step instructions for operating the device 10.

The software means may also control receiving and analyzing data collected by the device 10 and may display measurement results graphically on the computer display 350 or optionally print out the results on a printer 355. A series of results may be stored in storage 380 for further processing or recall. The device 10 may be controlled by means of an input, such as a keyboard 360 or a mouse 370, among many other possible input devices.

In summary, by generally limiting the device 10 to the essential components for providing a light source, and measuring the light which passes through a finger placed in the finger receptor 70, 140, the device 10 is significantly reduced in size and cost. Also, by significantly reducing the heat generated in the device, cooling requirements are reduced and the device 10 is less sensitive to heating problems, thereby improving the stability and accuracy of the device. Also, by transferring the control interface and analysis onto a computer 300, the processing power of the computer 300 is used to enhance the user interface and to enhance analysis of the raw data collected by the device 10.

While one embodiment of a device according to the present invention has been shown and described, it will be appreciated that changes and modifications are possible without departing from the scope of the invention which is defined by the following claims.

We claim:

1. A measuring device for non-invasively measuring levels of constituents in blood and tissue in a subject, the measuring device comprising:
   (a) a housing having an opening for receiving a hand of the subject;
   (b) a polychromatic light source that emits a broad spectrum of light in the near infrared range and adjacent visible light;
   (c) a part receptor shaped for receiving a finger of the subject, the part receptor being located relative to the light source so that when the finger of the subject is placed in the part receptor, the light source can be activated and light from the light source can be directed onto the finger, the part receptor being shaped to receive the finger in close alignment, so as to reduce extraneous light;
   (d) a light receptor for collecting a continuum of wavelengths over the broad spectrum of light after the broad spectrum of light has been directed onto the finger;
   (e) a dispersion element coupled to the light receptor for dispersing light collected by the light receptor into a dispersed spectrum of component wavelengths;
   (f) a photodetector coupled to the dispersion element for taking absorbance measurements from the dispersed spectrum and producing a measurement signal;
   (g) a communications interface connectable to an external computer for communicating the measurement signal to the external computer, and
   (h) a power interface connectable to an external stabilized power source.

2. The device of claim 1, further comprising a hand support at the housing opening, the hand support being adjustable to vary the size of the opening.

3. The device of claim 2, wherein the hand support receives the palm of a human hand and the top of the opening is curved to generally fit the profile of the human hand across the top of the hand.

4. The device of claim 1, wherein the polychromatic light source is connected to the power interface.

5. The device of claim 1, further comprising the external computer, wherein the external computer controls at least one function of the measuring device, the computer including means for receiving the measurement signal.

6. The device of claim 5, further comprising an analog to digital converter for converting the measurement signal into a digital measurement signal for communication to the computer.

7. The device of claim 5, wherein, the external computer includes a memory element, a storage element, and a software element for storing a plurality of measurement signals for a plurality of measurements.

8. The device of claim 5, wherein, sad the external computer includes a memory element, a storage element, and a software element for storing, retrieving and displaying dosage information corresponding to measurement signals received by the computer from the device.

9. The device of claim 5, further comprising the external stabilized power source.

10. The device of claim 9, wherein the external stabilized power source is provided by the external computer.

11. The device of claim 1, further comprising the external stabilized power source.

12. The device of claim 1, wherein the subject is a human or an animal.

* * * * *